US011266812B2

(12) United States Patent
Bedel

(10) Patent No.: US 11,266,812 B2
(45) Date of Patent: Mar. 8, 2022

(54) SMOKE EVACUATION TUBING ASSEMBLY

(71) Applicant: Aspen Surgical Products, Inc., Caledonia, MI (US)

(72) Inventor: David Lawrence Bedel, Oldenburg, IN (US)

(73) Assignee: Aspen Surgical Products, Inc., Caledonia, MI (US)

( * ) Notice: Subject to any disclaimer, the term of this patent is extended or adjusted under 35 U.S.C. 154(b) by 941 days.

(21) Appl. No.: 16/005,200

(22) Filed: Jun. 11, 2018

(65) Prior Publication Data

US 2018/0353730 A1    Dec. 13, 2018

Related U.S. Application Data

(60) Provisional application No. 62/518,410, filed on Jun. 12, 2017.

(51) Int. Cl.
| | | |
|---|---|---|
| *A61B 18/14* | (2006.01) | |
| *A61M 25/02* | (2006.01) | |
| *B32B 1/08* | (2006.01) | |
| *B32B 3/26* | (2006.01) | |
| *B32B 37/12* | (2006.01) | |
| *B32B 37/20* | (2006.01) | |
| *B32B 38/00* | (2006.01) | |
| *B32B 7/12* | (2006.01) | |

(Continued)

(52) U.S. Cl.
CPC ............... *A61M 25/02* (2013.01); *B32B 1/08* (2013.01); *B32B 3/266* (2013.01); *B32B 7/12* (2013.01); *B32B 37/10* (2013.01); *B32B 37/12* (2013.01); *B32B 37/203* (2013.01); *B32B 38/0004* (2013.01); *B32B 38/04* (2013.01); *A61M 2025/0246* (2013.01); *A61M 2025/0266* (2013.01); *A61M 2207/10* (2013.01); *B32B 2038/047* (2013.01); *B32B 2535/00* (2013.01)

(58) Field of Classification Search
CPC ......... A61B 18/14; A61B 20/03; A61B 20/00; A61B 22/00; A61M 1/00; A61M 27/00; A61M 25/02; A61M 2025/0246; A61M 2025/0266; A61M 2207/10; A61F 13/00; A61F 13/02; A61K 9/22; B32B 2038/047; B32B 2535/00
See application file for complete search history.

(56) References Cited

U.S. PATENT DOCUMENTS

| 5,015,243 A | 5/1991 | Schifano |
|---|---|---|
| 5,156,618 A | 10/1992 | Fiore et al. |

(Continued)

FOREIGN PATENT DOCUMENTS

WO    9316741 A1    9/1993

*Primary Examiner* — Tatyana Zalukaeva
*Assistant Examiner* — Ilya Y Treyger
(74) *Attorney, Agent, or Firm* — Price Heneveld LLP

(57) ABSTRACT

A smoke evacuation tubing assembly includes a base sheet having an adhesive disposed on a top side thereof. An elongate tubing member is operably coupled with a top side of the base sheet and includes a cross-section with first and second opposing rounded sidewalls and first and second generally planar sidewalls disposed between the first and second opposing rounded sidewalls. A plurality of apertures are defined through the first rounded sidewall. A central axis of each aperture is directed downwardly toward the top side of the base sheet. A cover sheet is operably coupled with the top side of the base sheet and is configured to engage the first generally planar sidewall of the elongate tubing member.

20 Claims, 7 Drawing Sheets

(51) Int. Cl.
   *B32B 37/10*   (2006.01)
   *B32B 38/04*   (2006.01)
   *A61M 1/00*    (2006.01)
   *A61F 13/00*   (2006.01)
   *A61F 13/02*   (2006.01)
   *A61M 27/00*   (2006.01)

(56) References Cited

U.S. PATENT DOCUMENTS

| | | |
|---|---|---|
| 5,211,639 A | 5/1993 | Wilk |
| 5,322,521 A | 6/1994 | Wilk |
| 5,941,873 A | 8/1999 | Korenfeld |
| 5,971,977 A | 10/1999 | Korenfeld |
| 6,942,650 B1 | 9/2005 | Schultz et al. |
| 2014/0058343 A1 | 2/2014 | Schultz |

# SMOKE EVACUATION TUBING ASSEMBLY

CROSS-REFERENCE TO RELATED APPLICATION

This application claims priority to and the benefit under 35 U.S.C. § 119(e) of U.S. Provisional Application No. 62/518,410, filed on Jun. 12, 2017, entitled "SMOKE EVACUATION TUBING ASSEMBLY" the disclosure of which is hereby incorporated herein by reference in its entirety.

FIELD OF THE DISCLOSURE

The present disclosure generally relates to a tubing assembly, and more particularly to a smoke evacuation tubing assembly.

SUMMARY OF THE DISCLOSURE

According to one aspect of the present disclosure, a smoke evacuation tubing assembly includes a base sheet having an adhesive disposed on a top side thereof. An elongate tubing member is operably coupled with a top side of the base sheet and includes a cross-section with first and second opposing rounded sidewalls and first and second generally planar sidewalls disposed between the first and second opposing rounded sidewalls. A plurality of apertures are defined through the first rounded sidewall. A central axis of each aperture is directed downwardly toward the top side of the base sheet. A cover sheet is operably coupled with the top side of the base sheet and is configured to engage the first generally planar sidewall of the elongate tubing member.

These and other features, advantages, and objects of the present disclosure will be further understood and appreciated by those skilled in the art by reference to the following specification, claims, and appended drawings.

DETAILED DESCRIPTION

Figure 1:
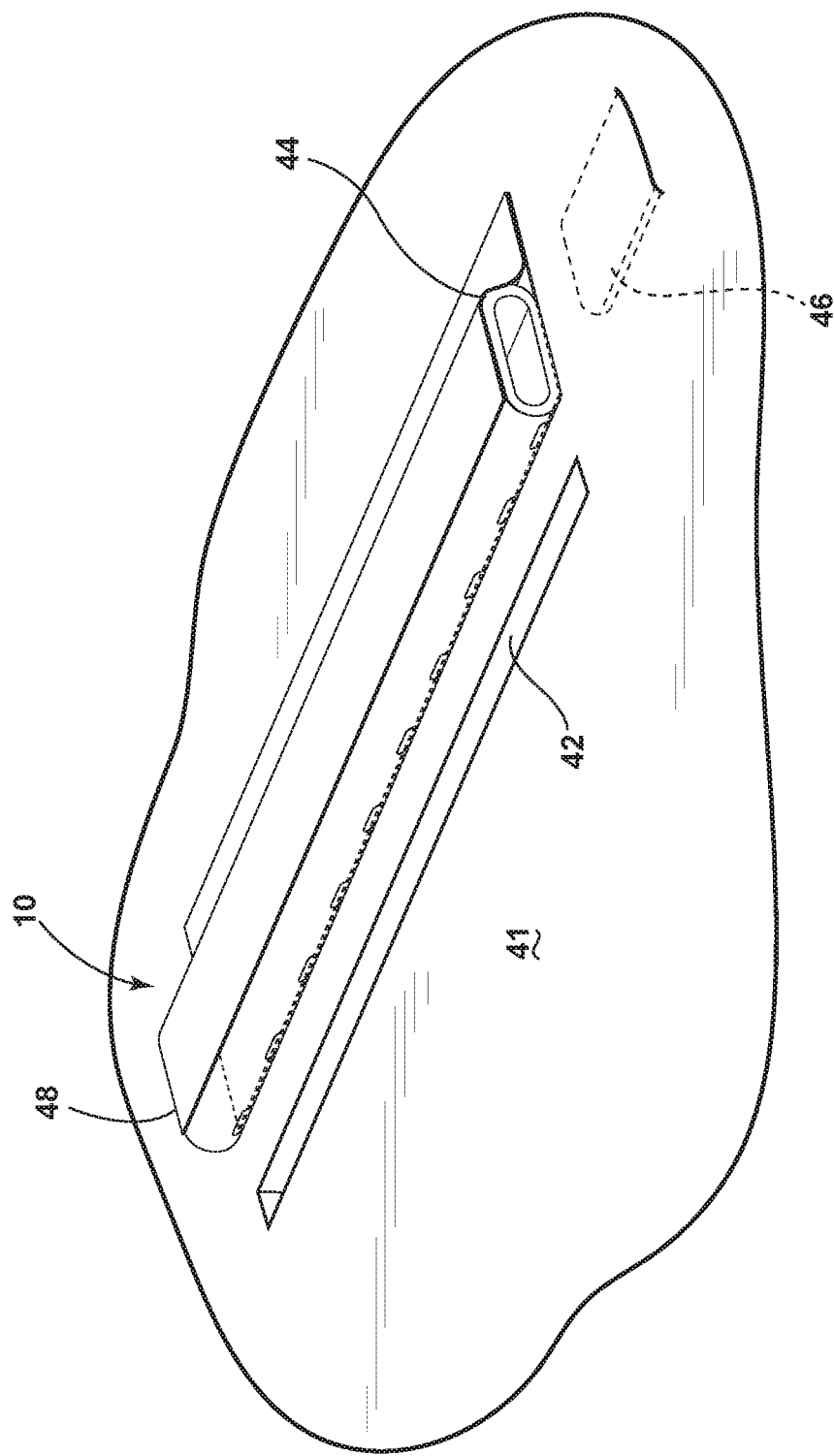
FIG. 1 is a top perspective view of a smoke evacuation tubing assembly of the present disclosure.

The present illustrated embodiments reside primarily in combinations of method steps and apparatus components related to a smoke evacuation tubing assembly. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to the surface of the device closer to an intended viewer of the device, and the term "rear" shall refer to the device further from the intended viewer of the device. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-7, reference numeral 10 generally designates a smoke evacuation tubing assembly having a base sheet 12 with an adhesive 14 disposed on a top side 16 thereof. An elongate tubing member 20 is operably coupled with the top side 16 of the base sheet 12 and includes a cross-section with first and second opposing rounded sidewalls 22, 24 and first and second generally planar sidewalls 26, 28 disposed between the first and second opposing rounded sidewalls 22, 24. A plurality of apertures 30 are defined through the first rounded sidewall 22. A central axis CA of each of the plurality of apertures 30 is directed downwardly toward the top side 16 of the base sheet 12. A cover sheet 32 is operably coupled with the top side 16 of the base sheet 12 and is configured to engage the first generally planar sidewall 26.

With reference again to FIG. 1, the smoke evacuation tubing assembly 10 is configured to withdraw and remove smoke 40 (FIGS. 5 and 6) of a surgical area 41 near an incision site 42 during a surgical procedure. The elongate tubing member 20 of the smoke evacuation tubing assembly 10 is elongate and generally configured to be placed adjacent to the incision site 42. However, it will be understood that the elongate tubing member 20 could be curved or otherwise bent to accommodate an incision that is not linear. In addition, it will be understood that the elongate tubing member 20 may be curved to follow any vertical contours of the incision. A proximal end 44 of the elongate tubing member 20 is configured to receive a male or female coupling 46, which may be a push-in connector, that connects with an existing smoke evacuation system disposed within the surgical suite. A distal end 48 of the elongate tubing member 20 may be sealed and crimped utilizing an ultrasonic welding technique. However, it will be understood that the elongate tubing member 20 may be closed via other manners, including heat staking, adhesive, coupling an end cap therewith, etc. As previously noted, the plurality of apertures 30 are defined through the first rounded sidewall 22. All or most of the first rounded sidewall 22 may be exposed. However, the first and second generally planar sidewalls 26, 28 may be substantially covered by the base sheet 12 and the cover sheet 32. In addition, the second opposing rounded sidewall 24 is also at least partially covered by the cover sheet 32. A portion of the base sheet 12 and the cover sheet 32 are operably coupled at a junction 50 proximate the second opposing rounded sidewall 24. A void 52 may be formed between the junction 50, second rounded sidewall 24, cover sheet 32, and base sheet 12. Alternatively, the base sheet 12 and cover sheet 32 may be adhered so that the junction 50 is abutting the second rounded sidewall 24.

Figure 2:
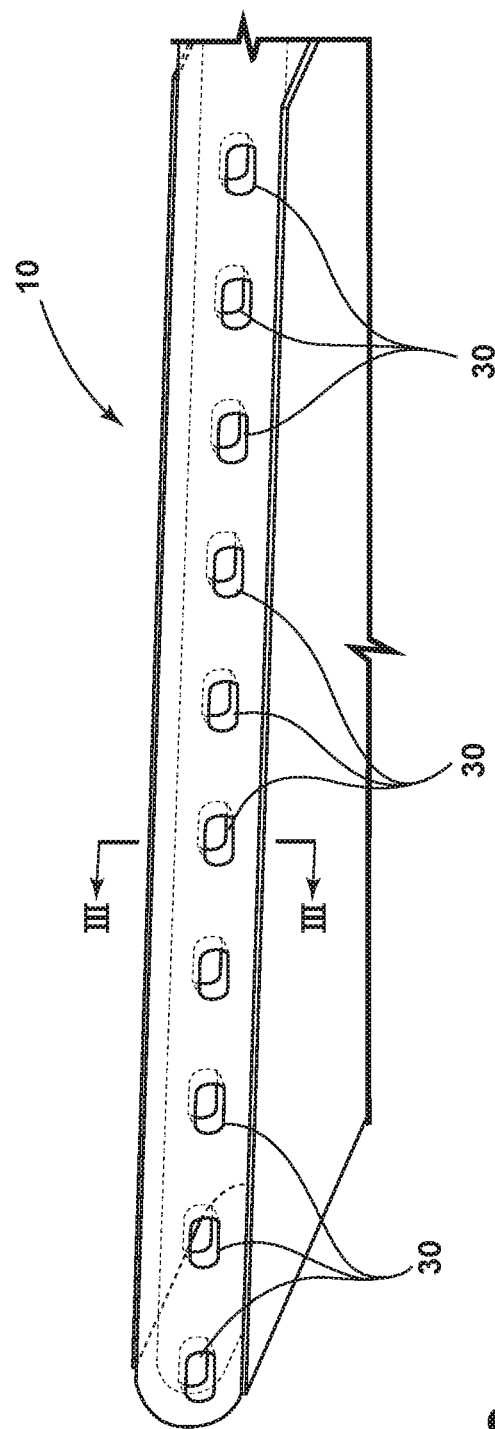
FIG. 2 is a bottom perspective view of the smoke evacuation tubing assembly of FIG. 1.
Figure 3:
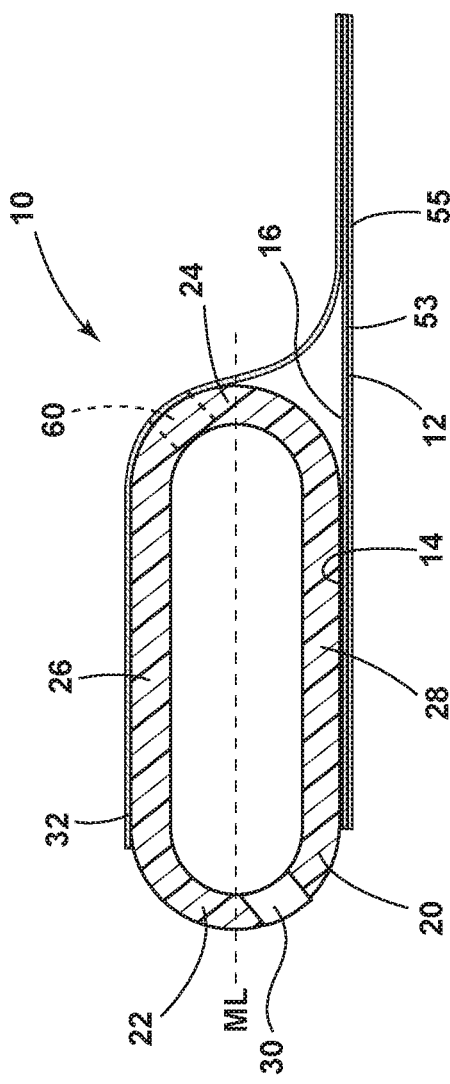
FIG. 3 is an enlarged cross-sectional elevational view of the smoke evacuation tubing assembly of FIG. 2 taken at III-III.
Figure 3A:
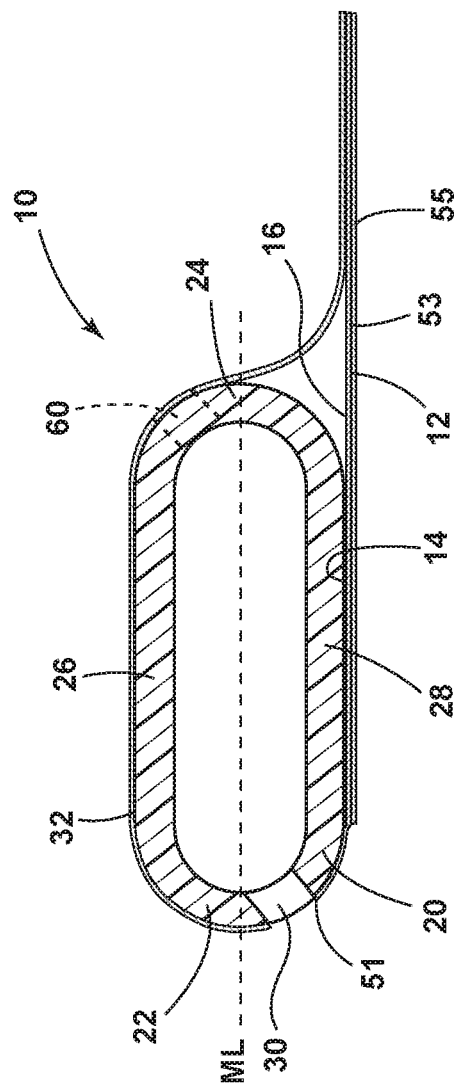
FIG. 3A is another enlarged cross-sectional elevational view of a smoke evacuation tubing assembly of the present disclosure.

In the illustrated embodiment shown in FIGS. 2 and 3, the plurality of apertures 30 that are defined through the first rounded sidewall 22 and the central axis CA of each of the plurality of apertures is directed at a downward angle ($\alpha$) of between 20 degrees and 60 degrees, and in some instances, approximately 39 degrees. However, it will be contemplated that the downward angle may be as great as 80 degrees or less than 5 degrees, depending on the application, the location of the incision site 42, the available space between the incision site 42 and the smoke evacuation tubing assembly 10, as well as other factors. As illustrated, the plurality of apertures 30 are generally disposed below a midline ML dissecting the elongate tubing member 20 into two generally equal halves. However, there may be instances where the plurality of apertures 30 are disposed at or above the midline ML. Further, as shown in FIG. 3A, the base sheet 12 and the cover sheet 32 may be integrally formed as one sheet that wraps around the elongate tubing member 20. In this instance, a plurality of openings 51 may be defined through the base sheet 12 or cover sheet 32 that coincide with the plurality of apertures 30 defined through the first rounded sidewall 22. Still further, the base sheet 12 may extend over a portion or all of the first rounded sidewall 22, but may not connect with the cover sheet 32. Alternatively, in this instance, the plurality of openings 51 will again coincide with the plurality of apertures 30.

Figure 4:
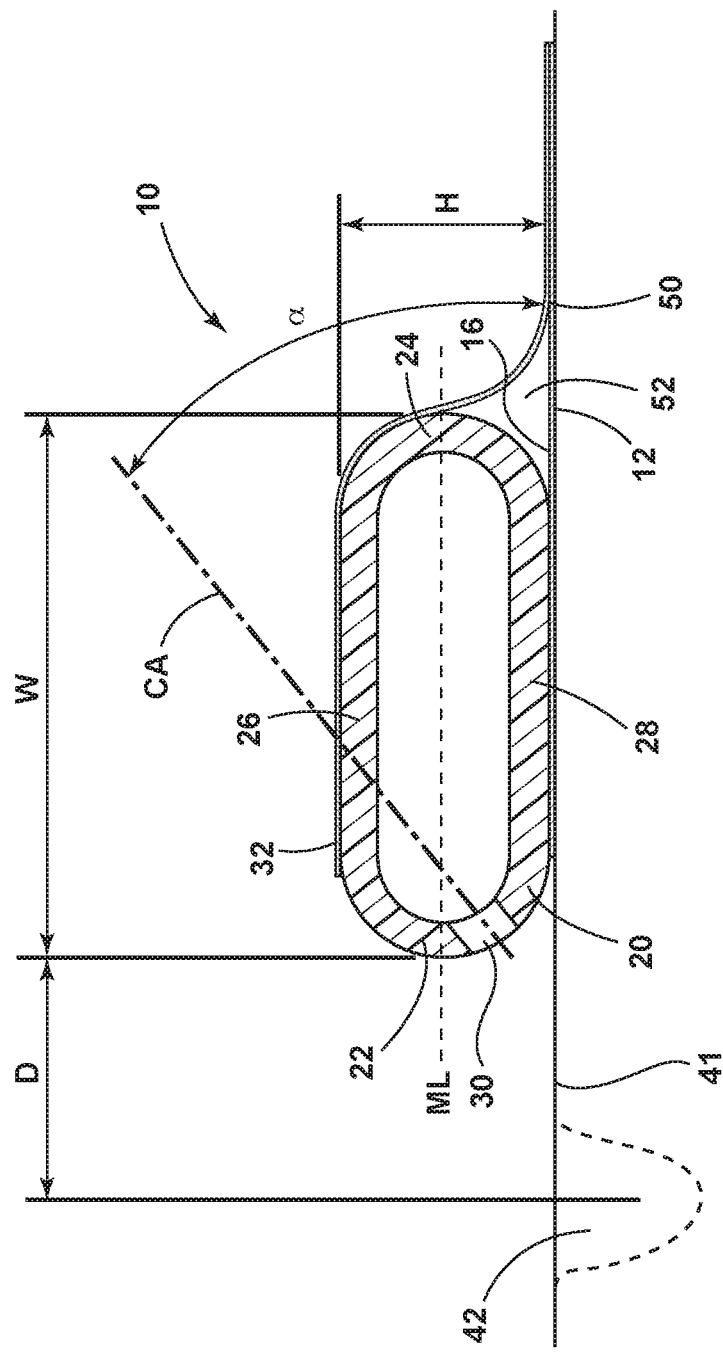
FIG. 4 is yet another enlarged cross-sectional elevational view of a smoke evacuation tubing assembly of the present disclosure.
Figure 5:
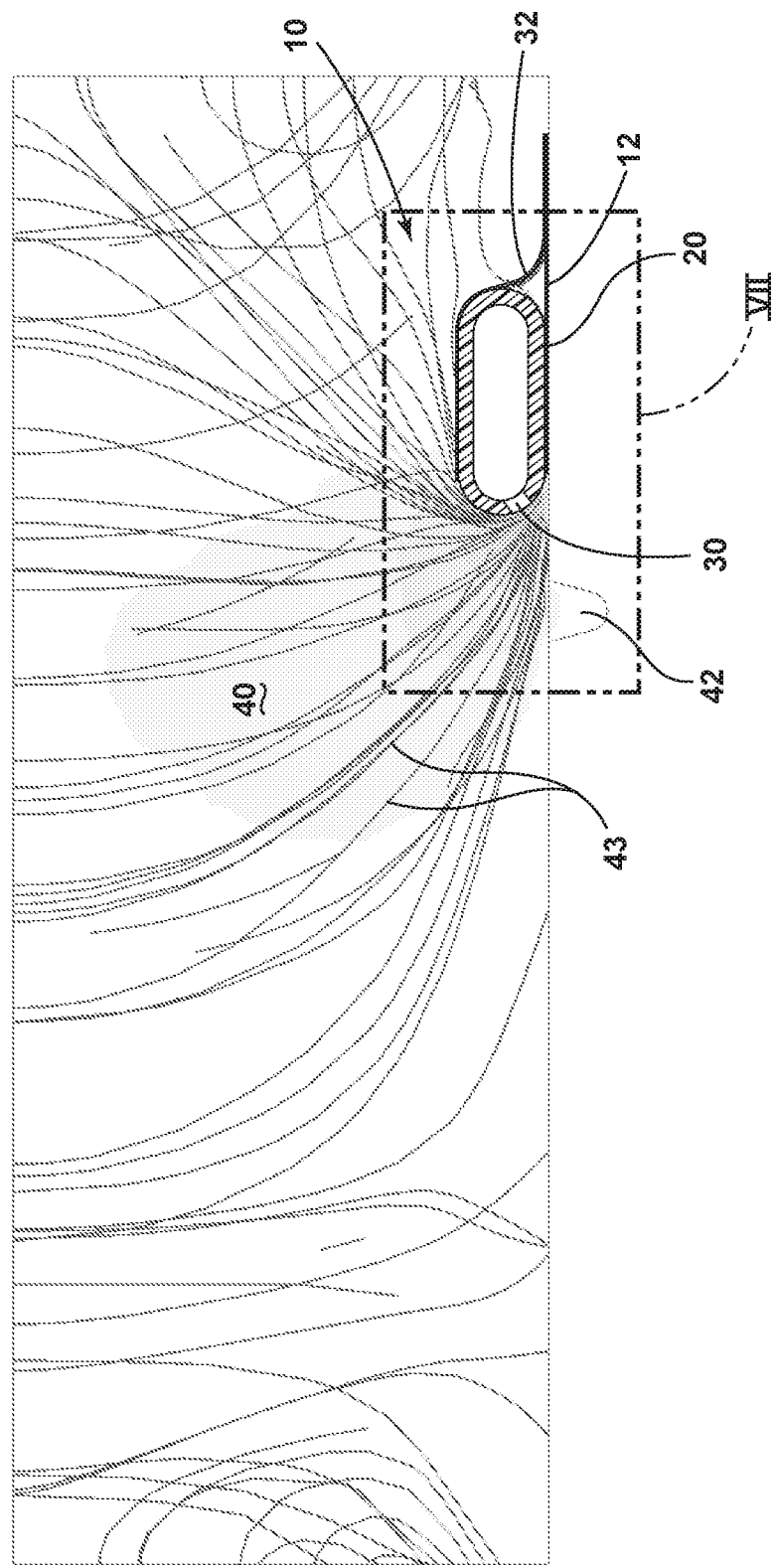
FIG. 5 is a side elevational view of a smoke evacuation tubing assembly of the present disclosure, illustrating airstreams of the device during use.
Figure 6:
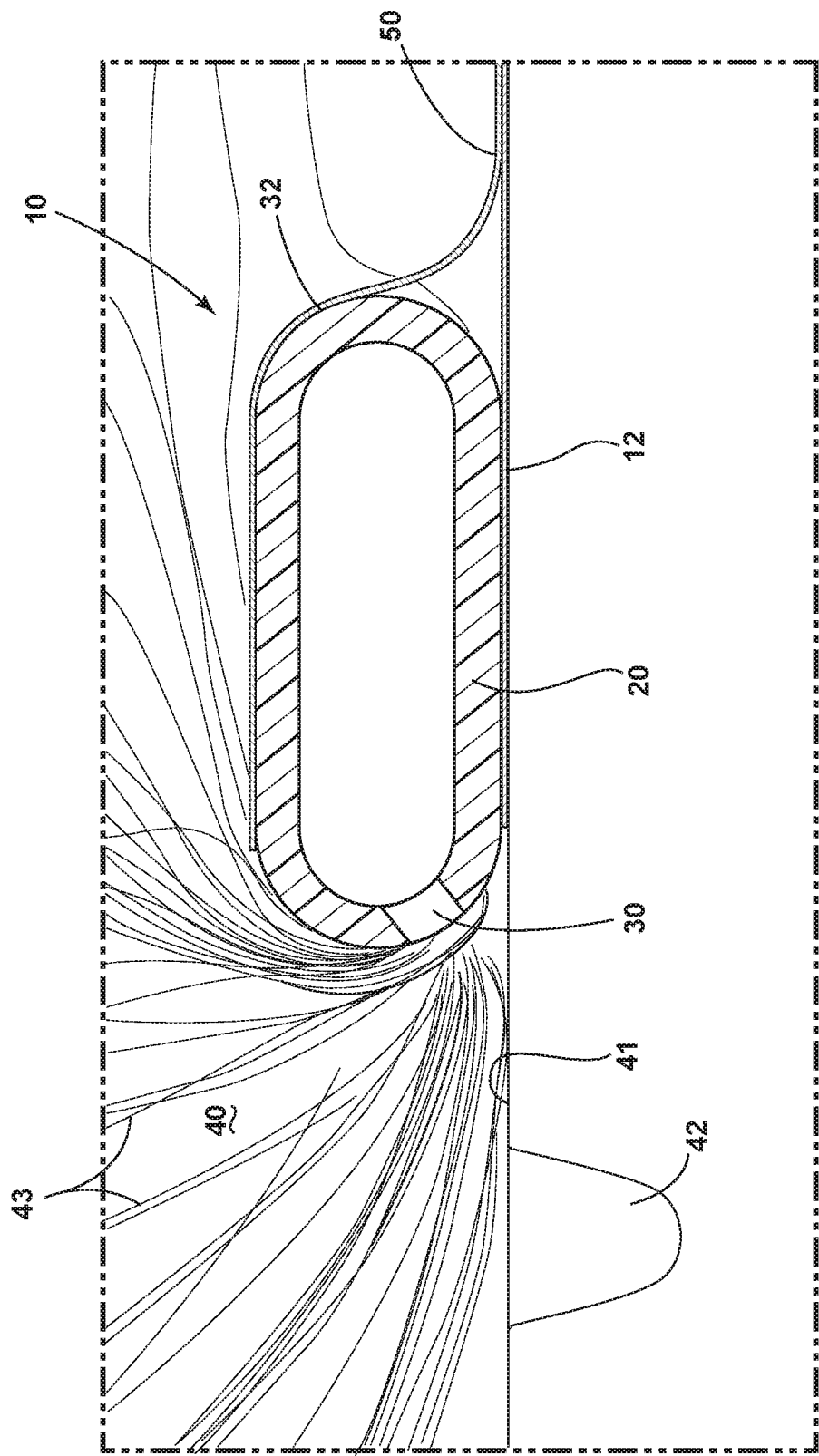
FIG. 6 is an enlarged view of the smoke evacuation tubing assembly of the area VI of FIG. 5.

In addition, as illustrated in FIGS. 3 and 4, it will be noted that a central axis CA of each of the plurality of apertures 30 intersects a portion of the surgical area 41 between the incision site 42 and the smoke evacuation tubing assembly 10. Stated differently, the incision site 42 is placed slightly beyond an intersection point of the central axis of each of the plurality of apertures 30 and a surface of the surgical area 41 of a patient. The smoke evacuation tubing assembly 10 may be secured or held in place on the skin of an individual by an adhesive 53 disposed on a bottom surface of the base sheet 12. A removable liner 55 may be removably coupled with a bottom of the base sheet 12. This configuration allows air and smoke to be drawn across the incision site 42 and from above the incision site 42 (designated by airflow lines 43). Location of the central axis (CA) of each of the plurality of apertures 30 in a position that intersects the incision site 42, or intersects a space beyond the incision site 42, may result in swirling, or otherwise could possibly interfere with a surgeon's view during the operation.

In one example, the smoke evacuation tubing assembly 10 is approximately ten inches long and includes 10-inch-$H_2O$ suction pressure from a smoke evacuation system. The smoke evacuation tubing assembly 10 includes the elongate tubing member 20 that is disposed a distance (D) between 2 mm and 20 mm, and in some instances may be approximately 9.3 mm away from a center of the incision site 42. The elongate tubing member 20 has a height (H) of approximately 8 mm and a width (W) of approximately 20.9 mm. It will be understood that these measurements are for illustrative purposes only and are not meant to be limiting. It will also be understood that variations to the construction will be understood by one having ordinary skill in the art.

With reference again to FIGS. 3 and 4, it will also be noted that the construction of the elongate tubing member 20 may include a second set of apertures 60 disposed through one of the first and second generally planar sidewalls 26, 28 or through the second rounded sidewall 24. The second set of apertures 60 may be disposed through the elongate tubing member 20 during the manufacturing process. In this instance, the apertures 30, 60 may be formed all the way through or punched all the way through the elongate tubing member 20. However, the second set of apertures 60 will be covered by one of the base sheet 12 and the cover sheet 32, resulting in the apertures 60 being closed. Accordingly, the second set of apertures 60 is unable to draw, vacuum, or move air in any way as one of the base sheet 12 and the cover sheet 32 prevents the same.

It will be generally understood that the size and location of the apertures 30 may also vary. In the illustrated embodiment, there are ten apertures 30 of similar size disposed along the elongate tubing member 20 and generally spaced equidistantly. However, it will be understood that the vacuum force may be strongest near the proximal end 44 of the elongate tubing member 20 and weakens closer to the distal end 48 of the elongate tubing member 20. Accordingly, it is generally contemplated that the plurality of apertures 30 may decrease in size as the plurality of apertures 30 extend from the proximal end 44 to the distal end 48, or may be spaced at greater intervals closer to the proximal end 44 to maintain a generally consistent negative pressure and airflow at each of the apertures 30. The plurality of apertures 30 may be spaced equidistantly or may have varying spacing concentrated more densely proximate a central portion of the incision cite. Alternatively, the plurality of apertures 30 may decrease in size and increase in spacing. Other variations, including the peripheral shape of the plurality of apertures 30 and number of the plurality of apertures 30 may also vary. In one example, the plurality of apertures are disposed below a midline extending between the first and second planar sidewalls and through at least one of the first and second opposing rounded sidewalls. In this instance, the apertures are elongated in a direction parallel with a longitudinal axis of the elongate tubing member.

The smoke evacuation tubing assembly 10, as set forth herein, is of significant benefit in a surgical suite. The use of the smoke evacuation tubing assembly 10 does not impact a surgeon's normal workflow and includes a low profile cross-section that allows access to the incision site 42 with minimal interference to the surgeon. In addition, the vertical and lateral flexible design conforms to the shape of a patient and moves with the incision site 42 during the surgical procedure. Adjustment of the smoke evacuation tubing assembly 10 is unnecessary, but in the event a surgeon wishes to adjust the location of the smoke evacuation tubing assembly 10, the device can simply be detached from the patient and adjusted. In addition, if additional vacuum is desired, surgical tape could be positioned over one or more of the plurality of apertures 30 to increase the suction at the remaining open plurality of apertures 30. The self-adhesive attachment of the smoke evacuation tubing assembly 10 and the push-in connector or coupling 46 that engages the proximal end 44 of the elongate tubing member 20 provides for easy and minimal setup time, allowing for the product to be easily disposed of upon completion of the surgical procedure.

Figure 7:
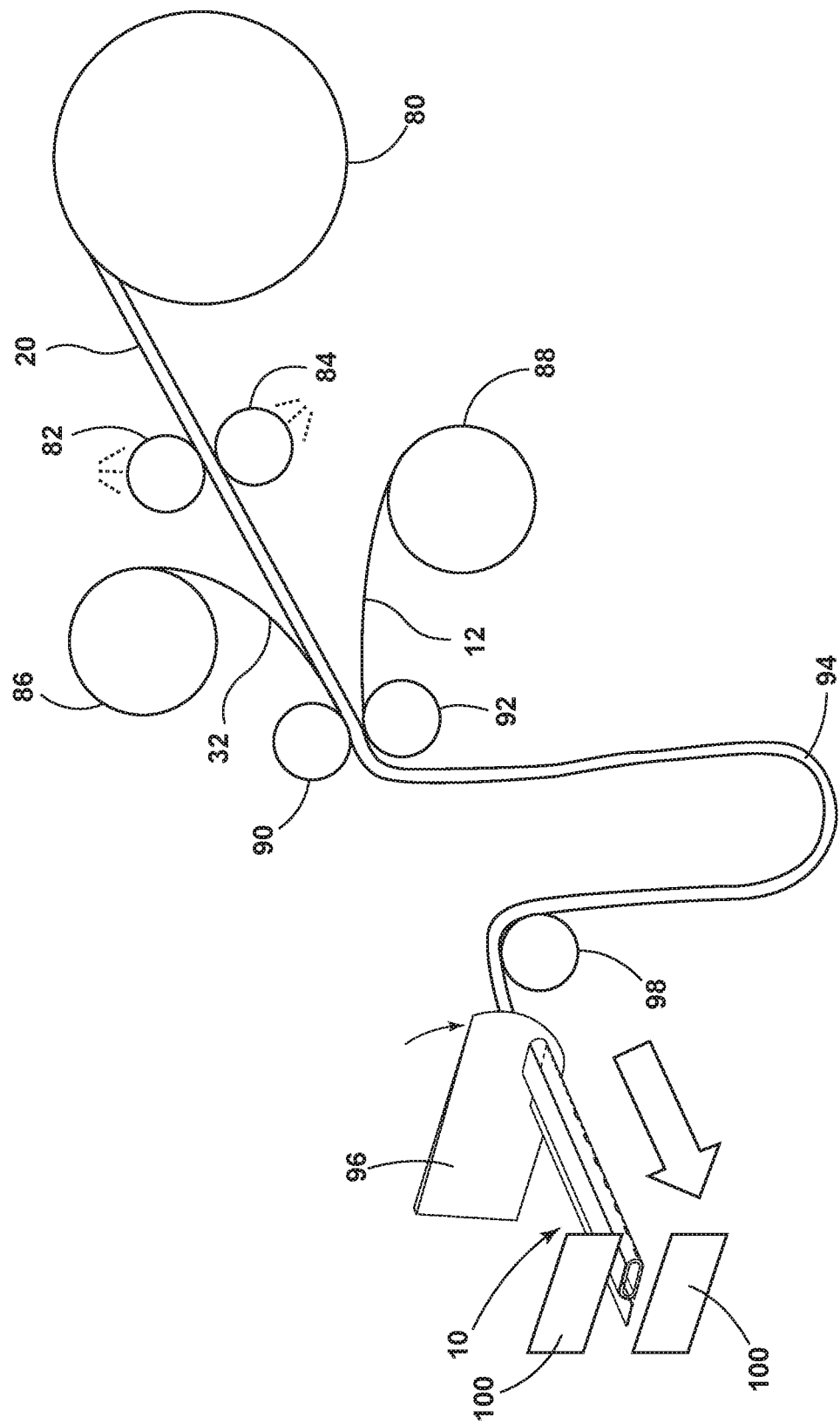
FIG. 7 is a schematic view of one embodiment of a manufacturing method for constructing a smoke evacuation tubing assembly.

With reference now to FIG. 7, during the manufacturing process, a roll of tubing 80 is unrolled and drawn through two adhesive application rollers 82, 84. After application of the adhesive 14, a top ply roller 86 and a bottom ply roller 88 will unroll to provide the cover sheet 32 and the base sheet 12, respectively. The base sheet 12, the elongate tubing member 20, and the cover sheet 32 are drawn through pinch rollers 90, 92, which seal the base sheet 12 with the cover sheet 32 and the elongate tubing member 20 between the base sheet 12 and the cover sheet 32. A predetermined volume of the elongate tubing member 20 is then disposed within an accumulator loop 94 and ultimately drawn past a blade 96, which cuts the elongate tubing member 20 at predetermined lengths. A perforation die 98, which cuts the plurality of apertures 30 into the elongate tubing member 20, is then activated to create the first set of the plurality of apertures 30, and possibly a second set of apertures 60, through the elongate tubing member 20. A crimp welder 100 then seals the distal end 48 of the elongate tubing member 20 and the finished smoke evacuation tubing assembly 10 is then placed in a sealed container for delivery. It will be understood that variations to this construction may also be applied. For example, the tubing 80 may include perforations disposed therethrough before unrolling. Alternatively, the tubing 80 may be unrolled, perforated, and then have the adhesive 14 applied by the adhesive application rollers 82, 84. Other variations are also possible and contemplated. For example, the perforation die 98 may punch into the elongate tubing member 20 from a side of the elongate tubing member 20. In this instance, the cut-off blade 96 and crimp welder 100 lower onto the elongate tubing member 20 and hold it in place while the perforation die 98 comes in from one side to make the plurality of apertures 30. The perforation die 98 may punch through one or more of the walls of the elongate tubing member 20.

In use, a surgeon may simply select the appropriate size of the smoke evacuation tubing assembly 10 that matches with the proposed incision length. A backing may be disposed on the base sheet 12 and is removed to expose the adhesive 14 on a bottom side of the base sheet 12. The smoke evacuation tubing assembly 10 is then aligned with the incision site 42 and the open end (proximal end 44) of the smoke evacuation tubing assembly 10 is operably coupled with the smoke evacuation system hose provided in the surgical suite. Normal draping of the surgical area 41 can then be completed.

By having a smoke evacuation tubing assembly that includes a low profile, increased vacuum can be provided close to the surgical site without interfering or complicating the efforts of a surgeon to make an incision. In addition, the unique alignment of the plurality of apertures 30 in the elongate tubing member 20 draws smoke and air across the incision site 42, thereby minimizing any impact on the view a surgeon has of the incision site 42, while also eliminating the smoke 40 from the surgical area 41.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A smoke evacuation tubing assembly comprising:
 a base sheet;
 an elongate linear tubing member operably coupled with a top side of the base sheet and including a cross-section with first and second opposing rounded sidewalls;
 a plurality of apertures defined through the first rounded sidewall, wherein a central axis of each aperture is directed downwardly; and a cover sheet operably coupled with the top side of the base sheet and configured to engage a first generally planar sidewall of the elongate tubing member.

2. The smoke evacuation tubing assembly of claim 1, wherein the central axis of each of the plurality of apertures is directed downwardly between 20 degrees and 60 degrees.

3. The smoke evacuation tubing assembly of claim 1, wherein the apertures are equidistantly spaced from one another.

4. The smoke evacuation tubing assembly of claim 1, wherein the first planar sidewall is completely covered by the cover sheet.

5. The smoke evacuation tubing assembly of claim 1, wherein the plurality of apertures are disposed below a midline extending between the first planar sidewall and a second planar sidewall and through at least one of the first and second opposing rounded sidewalls.

6. The smoke evacuation tubing assembly of claim 1, wherein the apertures are elongated in a direction parallel with a longitudinal axis of the elongate tubing member.

7. The smoke evacuation tubing assembly of claim 1, wherein the plurality of apertures includes a first set of open apertures and a second set of apertures closed by the cover sheet.

8. A smoke evacuation tubing assembly comprising:
a base sheet including an adhesive disposed on a top side thereof;
an elongate tubing member operably coupled with a top side of the base sheet and including a cross-section with first and second opposing rounded sidewalls and first and second generally planar sidewalls disposed between the first and second opposing rounded sidewalls;
a plurality of apertures defined through the first rounded sidewall, wherein a central axis of each aperture is directed downwardly; and
a cover sheet operably coupled with the top side of the base sheet and configured to engage the first generally planar sidewall of the elongate tubing member.

9. The smoke evacuation tubing assembly of claim 8, wherein the plurality of apertures are disposed below a midline extending between the first and second planar sidewalls and through at least one of the first and second opposing rounded sidewalls.

10. The smoke evacuation tubing assembly of claim 8, wherein the apertures are elongated in a direction parallel with a longitudinal axis of the elongate tubing member.

11. The smoke evacuation tubing assembly of claim 8, wherein the plurality of apertures includes a first set of open apertures and a second set of apertures closed by the cover sheet.

12. The smoke evacuation tubing assembly of claim 8, wherein the apertures are equidistantly spaced from one another.

13. The smoke evacuation tubing assembly of claim 8, wherein the first planar sidewall is completely covered by the cover sheet.

14. A smoke evacuation tubing assembly comprising:
a base sheet;
an elongate linear tubing member operably coupled with a top side of the base sheet and including a cross-section with first and second opposing rounded sidewalls;
a plurality of apertures defined through the first rounded sidewall, wherein a central axis of each aperture is directed downwardly; and
a cover sheet operably coupled with the top side of the base sheet and configured to engage a first generally planar sidewall of the elongate tubing member, wherein one of the base sheet and cover sheet extends over the plurality of apertures and wherein the one of the base sheet and cover sheet defines a plurality of openings that coincide with the plurality of apertures defined through the first rounded sidewall.

15. The smoke evacuation tubing assembly of claim 14, wherein the plurality of apertures are disposed below a midline extending between the first planar sidewall and a second planar sidewall and through the first and second planar sidewalls and through the first and second opposing rounded sidewalls.

16. The smoke evacuation tubing assembly of claim 14, wherein the apertures are elongated in a direction parallel with a longitudinal axis of the elongate tubing member.

17. The smoke evacuation tubing assembly of claim 14, wherein the plurality of apertures includes a first set of open apertures and a second set of apertures closed by the cover sheet.

18. The smoke evacuation tubing assembly of claim 14, wherein the base sheet includes an adhesive configured to secure said smoke evacuation tubing assembly to skin of an individual.

19. The smoke evacuation tubing assembly of claim 14, further comprising:
a removable liner operably coupled with a bottom side of the base sheet.

20. The smoke evacuation tubing assembly of claim 14, wherein the central axis of each of the plurality of apertures is directed downwardly between 20 degrees and 60 degrees.

* * * * *